(12) United States Patent
Minai et al.

(10) Patent No.: US 8,216,129 B2
(45) Date of Patent: Jul. 10, 2012

(54) IMAGE DISPLAY APPARATUS, ENDOSCOPE SYSTEM USING THE SAME, AND IMAGE DISPLAY METHOD

(75) Inventors: Tetsuo Minai, Hachioji (JP); Akio Uchiyama, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 580 days.

(21) Appl. No.: 12/533,442

(22) Filed: Jul. 31, 2009

(65) Prior Publication Data
US 2010/0030021 A1  Feb. 4, 2010

(30) Foreign Application Priority Data
Jul. 31, 2008 (JP) ................. 2008-198882

(51) Int. Cl.
*A61B 1/04* (2006.01)
*G09C 5/00* (2006.01)
*H04N 7/18* (2006.01)
(52) U.S. Cl. ............. 600/118; 348/71; 345/634
(58) Field of Classification Search .......... 600/118; 348/65, 71; 345/624, 634
See application file for complete search history.

(56) References Cited

U.S. PATENT DOCUMENTS

| | | | | |
|---|---|---|---|---|
| 5,031,036 A * | 7/1991 | Kikuchi et al. | ............ | 348/71 |
| 6,339,446 B1 * | 1/2002 | Miyoshi | ............ | 348/65 |
| 7,324,674 B2 * | 1/2008 | Ozawa et al. | ............ | 382/128 |
| 7,609,905 B2 * | 10/2009 | Conrad et al. | ............ | 382/254 |
| 8,107,768 B2 * | 1/2012 | Nomoto | ............ | 382/282 |
| 2004/0186351 A1 * | 9/2004 | Imaizumi et al. | ............ | 600/160 |
| 2005/0167621 A1 | 8/2005 | Zeng et al. | | |
| 2006/0100526 A1 | 5/2006 | Yamamoto et al. | | |
| 2006/0256191 A1 * | 11/2006 | Iketani et al. | ............ | 348/65 |
| 2007/0167754 A1 | 7/2007 | Okuno et al. | | |
| 2008/0030578 A1 | 2/2008 | Razzaque et al. | | |
| 2008/0231692 A1 * | 9/2008 | Higuchi et al. | ............ | 348/65 |
| 2012/0002026 A1 * | 1/2012 | Honda et al. | ............ | 348/65 |

FOREIGN PATENT DOCUMENTS

| | | |
|---|---|---|
| JP | 2005-296200 | 10/2005 |
| JP | 2006-305369 | 11/2006 |
| JP | 2007-319442 | 12/2007 |

OTHER PUBLICATIONS

Extended Partial European Search Report dated Nov. 30, 2009.

\* cited by examiner

*Primary Examiner* — W. B. Perkey
(74) *Attorney, Agent, or Firm* — Scully, Scott, Murphy & Presser, P.C.

(57) ABSTRACT

An image display apparatus according to the present invention includes: a storage unit which stores an image group including a same number of first and second images which have a coincident positional relationship with respect to a subject and are respectively obtained through different image processes; a display unit which displays at least the first image in a display area; an input unit which indicates a display switching area of the first image displayed in the display area; and a display controller which controls the display unit to keep displaying the first image in an image part outside the display switching area and to switch an image part inside the display switching area of the first image to an image part, having a coincident positional relationship with the image part inside the display switching area of the first image with respect to the subject, of the second image.

18 Claims, 9 Drawing Sheets

(SWITCHED DISPLAY MODE)

(NORMAL DISPLAY MODE)

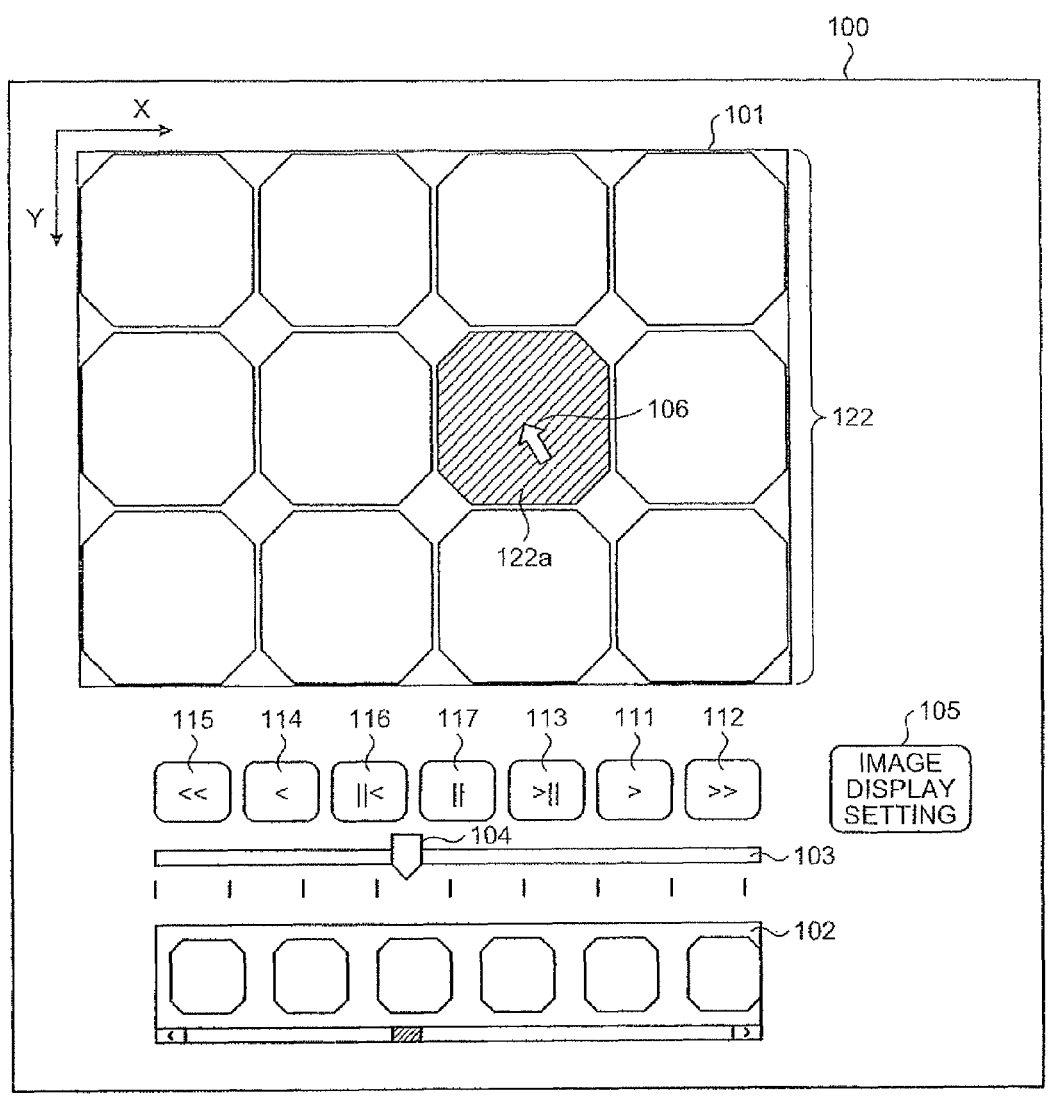

IMAGE DISPLAY APPARATUS, ENDOSCOPE SYSTEM USING THE SAME, AND IMAGE DISPLAY METHOD

CROSS-REFERENCE TO RELATED APPLICATIONS

This application is based upon and claims the benefit of priority from Japanese Patent Application No. 2008-198882, filed on Jul. 31, 2008, the entire contents of which are incorporated herein by reference.

BACKGROUND OF THE INVENTION

1. Field of the Invention

The present invention relates to an image display apparatus which displays images of an inside of an organ of a subject, an endoscope system using the same, and an image display method.

2. Description of the Related Art

Conventionally, an endoscope system in which an image of an inside of organs (hereinafter sometimes referred to as an "in-vivo image") obtained by inserting a capsule endoscope as a swallowable endoscope into the inside of organs of a subject is displayed has been proposed in the field of an endoscope. The capsule endoscope is provided with an imaging function and a wireless communication function inside a capsule-shaped casing. The capsule endoscope is taken into the subject through a mouth for the purpose of an observation of the inside of organs of the subject such as a patient, travels the inside of organs according to their peristalsis, and is eventually excreted to outside of the subject. The capsule endoscope captures in-vivo images at 0.5-second intervals, for example, during a period which starts when it is swallowed from the mouth of the subject and ends when it is naturally excreted to the outside of the subject, and wirelessly transmits the obtained in-vivo images to the outside of the subject sequentially.

In-vivo images wirelessly transmitted from the capsule endoscope along time series are sequentially received by a receiver placed outside the subject. The receiver stores an in-vivo image group received along time series from the capsule endoscope in a recording medium which is attached in advance. The recording medium in the receiver, after storing substantially the in-vivo image group captured by the capsule endoscope, is detached from the receiver and attached to an image display apparatus. The image display apparatus imports the in-vivo image group in the attached recording medium and sequentially displays each of the obtained in-vivo images on a display. Doctors, nurses, or the like can observe each in-vivo image sequentially displayed in the image display apparatus and observe (examine) the inside of organs of the subject through the observation of the in-vivo images.

As such an image display apparatus, a technique of dividing an image stream capture by a capsule endoscope into a plurality of image streams and displaying the plurality of image streams on a display virtually at once is disclosed in Japanese Patent Application Laid-Open No. 2006-305369, for example. In addition, a technique of adjusting, to a desired hue, an image within a correction frame which is displayed on a display screen and correcting color variability due to a difference in a color of a mucus membrane of each patient is disclosed in Japanese Patent Application Laid-Open No. 2005-296200, for example.

SUMMARY OF THE INVENTION

An image display apparatus according to one aspect of the present invention includes: a storage unit which stores an image group including a same number of first and second images which have a coincident positional relationship with respect to a subject and are respectively obtained through different image processes; a display unit which displays at least the first image in a display area; an input unit which indicates a display switching area of the first image displayed in the display area; and a controller which controls the display unit to keep displaying the first image in an image part outside the display switching area and to switch an image part inside the display switching area of the first image to an image part, having a coincident positional relationship with the image part inside the display switching area of the first image with respect to the subject, of the second image.

An endoscope system according to another aspect of the present invention includes: an endoscope device which captures an in-vivo image of a subject; an image generator which generates a first image and a second image which have a coincident positional relationship with respect to the subject and are respectively obtained through different image processes based on color data of one frame in-vivo image captured by the endoscope device; a display unit which displays at least the first image in a display area; an input unit which indicates a display switching area of the first image displayed in the display area; and a controller which controls the display unit to keep displaying the first image in an image part outside the display switching area and to switch an image part inside the display switching area of the first image to an image part, having a coincident positional relationship with the image part inside the display switching area of the first image with respect to the subject, of the second image.

An image display method according to still another aspect of the present invention includes: generating a first image and a second image which have a coincident positional relationship with respect to a subject and are respectively obtained through different image processes; and displaying the first image in an image part outside a display switching area in a display unit and switching an image part inside the display switching area to an image part, having a coincident positional relationship with the image part inside the display switching area of the first image with respect to the subject, of the second image.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is a view of a specific example of a display window in a case of displaying a plurality of in-vivo images with index in the embodiment of the present invention.

DETAILED DESCRIPTION OF THE PREFERRED EMBODIMENTS

Exemplary embodiments of an image display apparatus, an endoscope system using the same, and an image display method according to the present invention will be explained in detail below with reference to the accompanying drawings. It should be noted that though a capsule endoscope is taken as an example of an endoscope device in the endoscope system according to the present invention below, the present invention is not limited to the embodiments.

Figure 1:
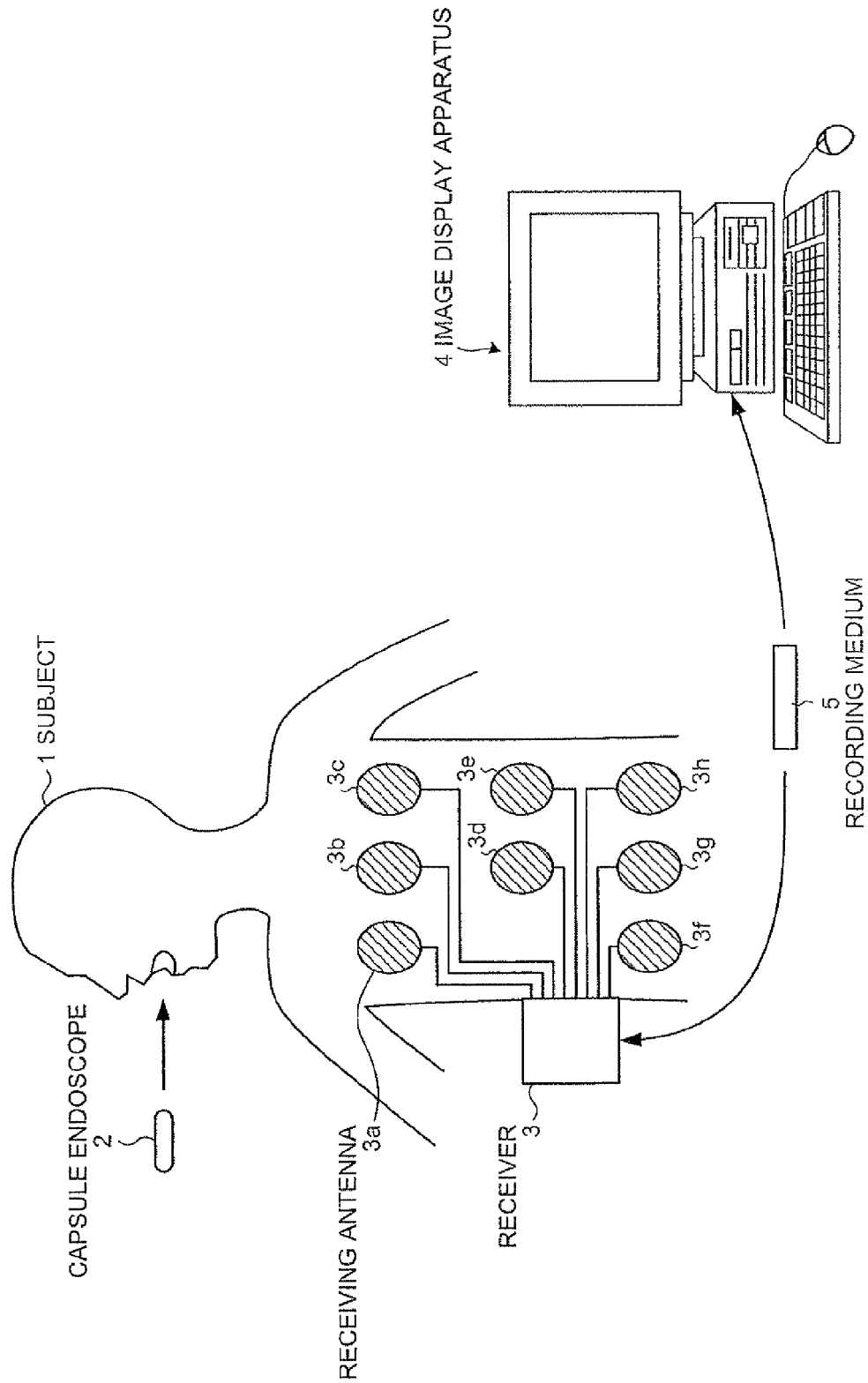
FIG. 1 is a view of an example of a structure of an endoscope system according to an embodiment of the present invention.

FIG. 1 is a view of an example of a structure of an endoscope system according to an embodiment of the present invention. As shown in FIG. 1, the endoscope system according to the embodiment includes: a capsule endoscope 2; a receiver 3; an image display apparatus 4; and a portable recording medium 5. The capsule endoscope 2 is inserted into an inside of a subject 1 through a mouse and the like, and captures an in-vivo image group of the subject 1. The receiver 3 receives an image signal wirelessly transmitted from the capsule endoscope 2. The image display apparatus 4 displays the in-vivo image group captured by the capsule endoscope 2. The recording medium 5 is used by a user for transferring data between the receiver 3 and the image display apparatus 4.

The capsule endoscope 2 is an example of an endoscope device which captures in-vivo images of the subject 1 and has an imaging function and a wireless communication function inside a capsule-shaped casing. The capsule endoscope 2 is inserted into an inside of organs of the subject 1 via a mouth and the like, and then sequentially captures in-vivo images of the subject 1 at predetermined intervals (at 0.5-second intervals, for example) while traveling the inside of the organs of the subject 1 according to their peristalsis. Specifically, the capsule endoscope 2 irradiates a subject to be imaged inside the organs with illumination light such as white light and captures an image of the subject illuminated by the illumination light, i.e., an in-vivo image of the subject 1. The capsule endoscope 2 wirelessly transmits an image signal of the in-vivo image of the subject 1 captured in this manner to the receiver 3 placed outside. The capsule endoscope 2 sequentially repeats the operation of capturing in-vivo images and the operation of wirelessly transmitting image signals of the captured in-vivo images during a period which starts when it is inserted into the inside of organs of the subject 1 and ends when it is excreted to the outside of the subject 1.

The receiver 3 includes a plurality of receiving antennas 3a to 3h which are, for example, dispersed and arranged on a body surface of the subject 1 and receives a wireless signal from the capsule endoscope 2 inside the subject 1 via at least one of the plurality of receiving antennas 3a to 3h. The receiver 3 extracts an image signal from the wireless signal transmitted from the capsule endoscope 2 and obtains image data of the in-vivo image contained in the extracted image signal.

Besides, the receiver 3 has an image generating function of generating two kinds of images which have a coincident positional relationship with respect to the subject through different image processes. Specifically, the receiver 3 performs different image processes based on color data of an in-vivo image for one frame obtained from the capsule endoscope 2 to generate two kinds of images, a white light image (hereinafter treated as a "first image") and a spectral image (hereinafter treated as a "second image"), for example, which have a coincident positional relationship with respect to the subject and are obtained respectively through different image processes. The white light image and the spectral image generated by the receiver 3 are in-vivo images which are different from each other in graphic mode and which are obtained from the same subject. Whenever the receiver 3 obtains one frame in-vivo image from the capsule endoscope 2, the receiver 3 sequentially generates the white light image and the spectral image capturing the same subject based on the obtained one frame in-vivo image. The receiver 3 stores a white light image group and a spectral image group in the recording medium 5 attached in advance. In this case, the receiver 3 sequentially stores the white light image and the spectral image capturing the same object based on the same in-vivo image as in-vivo images whose image processes are different from each other and which have the same frame number in the recording medium 5. In addition, the receiver 3 associates time data such as an imaging time or a reception time of an original in-vivo image with each image of the white light image group and the spectral image group.

The white light image is a color image of a subject illuminated by white light and is useful for a normal image observation. On the other hand, the spectral image is an image generated based on a specific color component such as a green color and a blue color and can emphatically depict a state of the inside of organs such as a capillary blood vessel in a superficial layer of a mucus membrane, a deep blood vessel, and a concave/convex part like a lesion site and the like of body tissues, which cannot be easily recognized visually in the white light image. The comparison of the area of interest in the in-vivo image with a switched image such as the white light image and the spectral image respectively obtained via different image processes is useful for a detailed observation, like a visual recognition of whether or not a pathognomonic site such as a bleeding site and a lesion site is present in the area of interest, of the area of interest.

The receiving antennas 3a to 3h of the receiver 3 may be arranged on the body surface of the subject 1 as shown in FIG. 1 or may be arranged on a jacket to be worn by the subject 1. It should be noted that it is only necessary that the number of antennas of the receiver 3 be at least one and the number is not specifically limited to eight.

The image display apparatus 4 has a configuration like a workstation which imports various kinds of data such as the in-vivo image group of the subject 1 via the recording medium 5 and displays various kinds of data such as the imported in-vivo image group. Specifically, when the recording medium 5 detached from the receiver 3 is attached thereto, the image display apparatus 4 imports data stored in the recording medium 5 and thereby obtains various kinds of data such as the in-vivo image group of the subject 1 (the white light image group and the spectral image group described above, for example). The image display apparatus 4 has a function of displaying an obtained in-vivo image on a display and switching a desired image area specified in the displayed in-vivo image to an image which captures the same subject and is obtained via a different image process. A detailed structure of the image display apparatus 4 will be explained later.

The recording medium 5 is a portable recording medium for transferring data between the receiver 3 and the image display apparatus 4. The recording medium 5 can be detachably attached to the receiver 3 and the image display apparatus 4, and has a structure of enabling outputting and recording data when attached to the devices. Specifically, the recording medium 5, when attached to the receiver 3, records the in-vivo image group to which an image process is performed by the receiver 3, time data of each image, and the like. Here, as the in-vivo image group obtained through the image process by the receiver 3, the white light image group and the spectral image group which have a coincident positional relationship with respect to the subject between images having the same frame number can be listed. On the other hand, when the recording medium 5 detached from the receiver 3 is attached to the image display apparatus 4, the data (the in-vivo image group and the like) stored in the recording medium 5 is imported to the image display apparatus 4.

Figure 2:
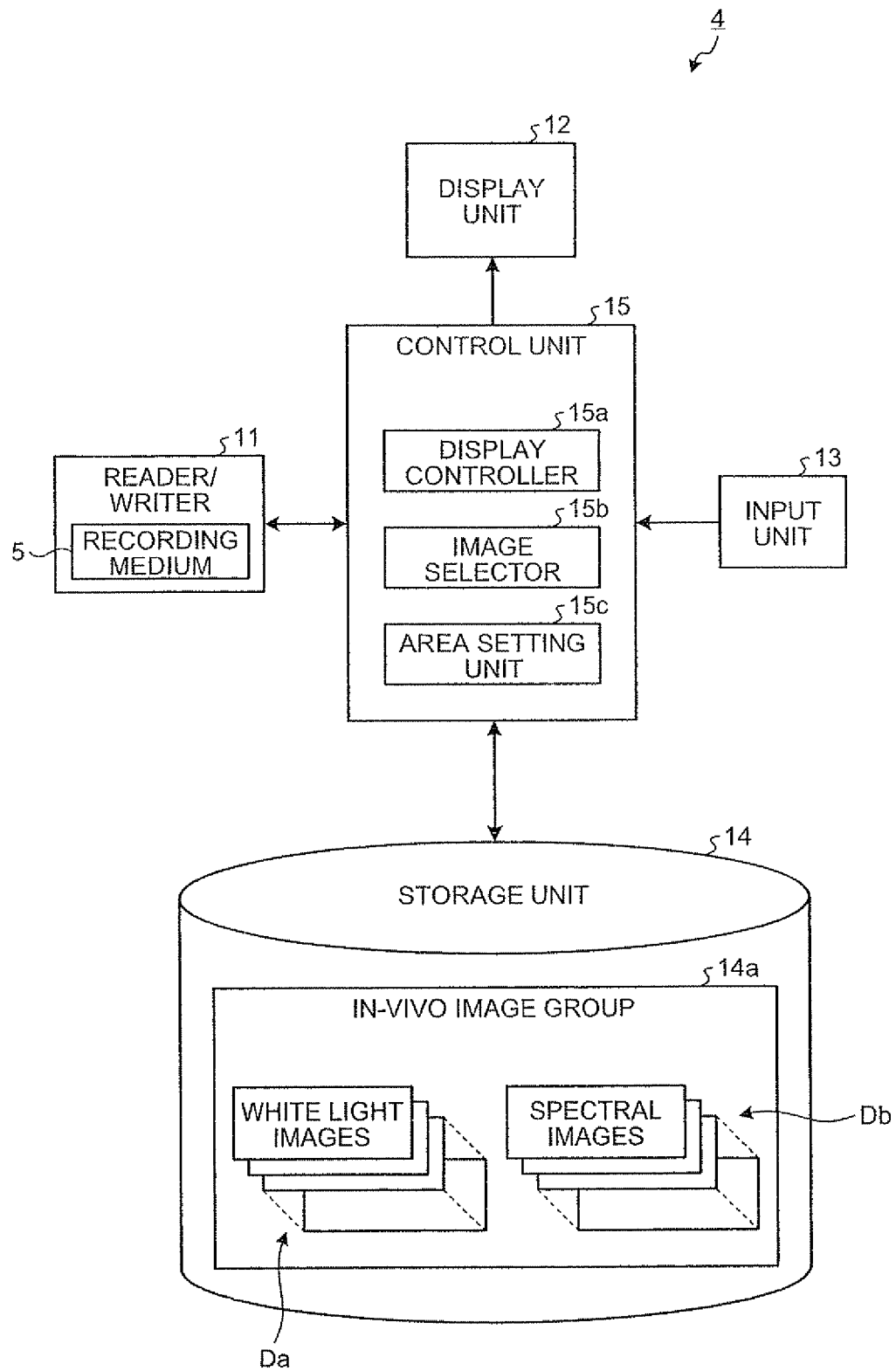
FIG. 2 is a block diagram schematically showing an example of a structure of an image display apparatus according to the embodiment of the present invention.

Next, a structure of the image display apparatus 4 according to the embodiment of the present invention will be explained in detail. FIG. 2 is a block diagram schematically showing an example of a structure of the image display apparatus according to the embodiment of the present invention. As shown in FIG. 2, the image display apparatus 4 according to the embodiment includes a reader/writer 11, a display unit 12, an input unit 13, a storage unit 14, and a control unit 15. The reader/writer 11 imports data stored in the recording medium 5 described above. The display unit 12 displays in-vivo images of the subject 1, a graphical user interface (GUI), and the like on a screen. The input unit 13 inputs various kinds of information. The storage unit 14 stores data imported by the reader/writer 11 and the like. The control unit 15 controls constituent units of the image display apparatus 4.

The reader/writer 11, to which the recording medium 5 detached from the receiver 3 is detachably attached, imports the data stored in the recording medium 5 and transfers the imported storage data to the control unit 15. In addition, the reader/writer 11, to which initialized recording medium 5 is attached, writes data which the control unit 15 instructs the reader/writer 11 to write into the recording medium 5. As the data to be imported by the reader/writer 11 from the recording medium 5, an in-vivo image group 14a of the subject 1 (more specifically, a white light image group Da and a spectral image group Db which have a coincident positional relationship with respect to the subject between images having the same frame number), time data of each in-vivo image, and the like can be listed, for example. On the other hand, as data to be written by the reader/writer 11 into the recording medium 5, data such as a patient name, a patient ID, and the like which identifies the subject 1 can be listed, for example.

Figure 3:
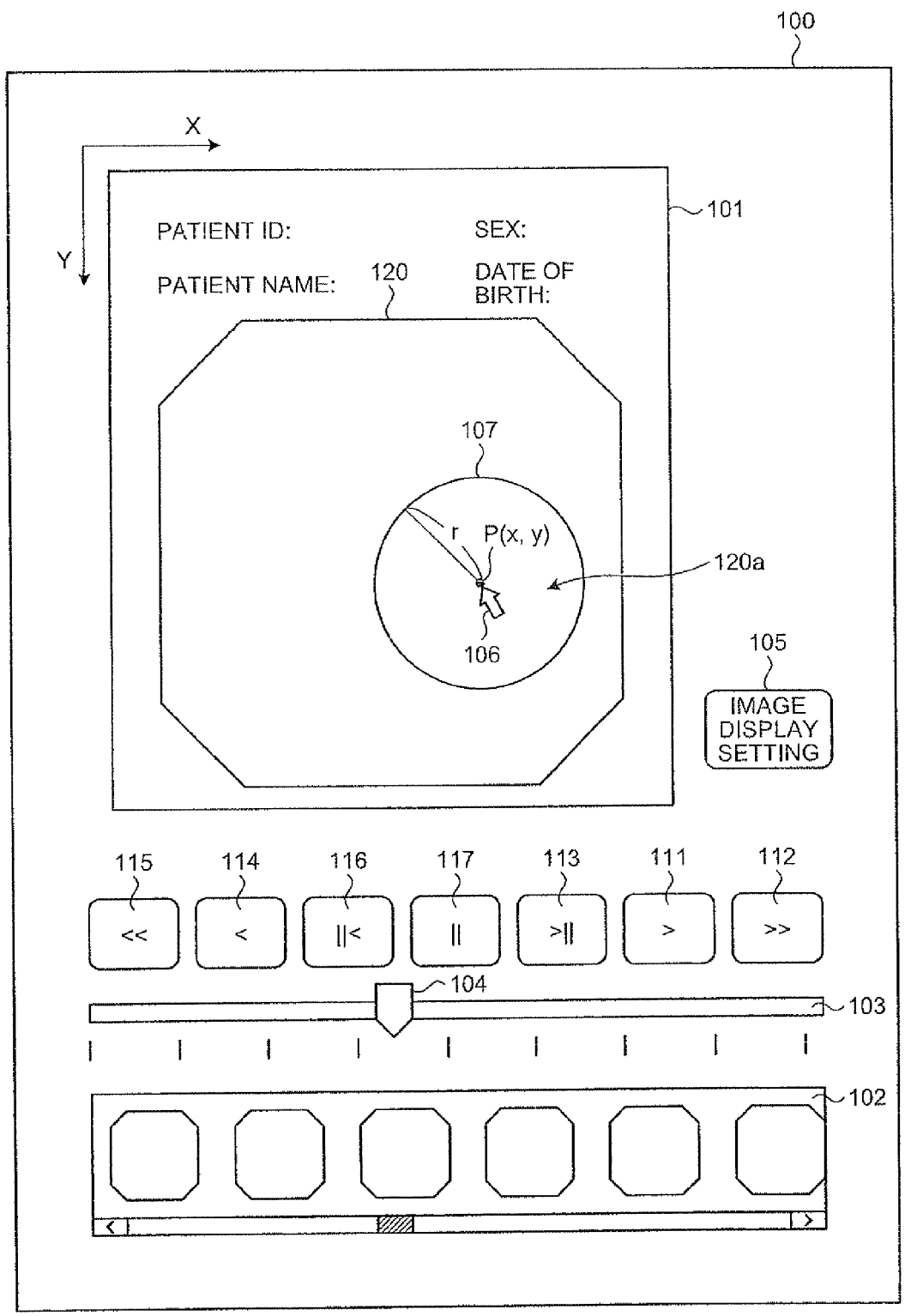
FIG. 3 is a view of a specific example of a display mode in a display unit according to the embodiment of the present invention.

The display unit 12 is realized by using a display device capable of displaying images such as a cathode-ray tube display and a liquid crystal display, and displays various kinds of information including in-vivo images and the like which the control unit 15 instructs the display unit 12 to display. FIG. 3 is a view of a specific example of a display mode in the display unit 12. The display unit 12 displays a display window 100 as shown in FIG. 3 in displaying an in-vivo image of the subject 1. In the display window 100, a main display area 101 as an area which displays an in-vivo image is formed. The display unit 12 displays a normal image 120 which is an in-vivo image to be normally displayed as a pseudo moving image or a still image in the main display area 101. In addition, the display unit 12, when a display switching area 107 is specified in the main display area 101, displays an image area in the display switching area 107 by changing over from the normal image 120 to a differently-processed image 120a. Here, the differently-processed image 120a is an in-vivo image which is generated via an image process different from that performed on the normal image 120 and has a coincident positional relationship with respect to the subject with the image part inside the display switching area 107 in the normal image 120. In other words, the normal image 120 and the differently-processed image 120a are in-vivo images which are obtained through different image processes respectively and have a coincident positional relationship with respect to the subject, and specifically which are the white light image and the spectral image based on the same in-vivo image described above.

Besides, the display unit 12 may display data for specifying the subject 1 (specifically, the patient ID, patient name, sex, date of birth, and the like) corresponding to the in-vivo image as the normal image 120 currently displayed in the main display area 101 as shown in FIG. 3.

In addition, in the display window 100 of the display unit 12, a display subarea 102 which displays reduced-size images such as thumbnail images which are reduced-size in-vivo images is formed. The display unit 12, whenever a desired in-vivo image is selected from in-vivo images each displayed as the normal image 120 in the main display area 101, sequentially adds and displays a reduced-size image of the selected desired in-vivo image in the display subarea 102. Besides, the display unit 12 displays various kinds of GUIs in the display window 100. Specifically, the display unit 12 displays a time bar 103, a slider 104, an image display setting icon 105, and display operation icons 111 to 117. The time bar 103 indicates a general temporal position of each in-vivo image displayed as the normal image 120 in the main display area 101. The slider 104 moves along the time bar 103 and indicates a temporal position of the normal image 120 currently displayed in the main display area 101. The image display setting icon 105 is a GUI for performing various kinds of settings regarding an image display. The display operation icons 111 to 117 are GUIs for performing a display operation of an in-vivo image as the normal image 120. In addition, the display unit 12 displays a pointer 106 (sometimes referred to as a "mouse pointer") which moves in response to an operation of the input unit 13.

Specifically, the display operation icon 111 among the display operation icons 111 to 117 displayed in the display window 100 is a GUI for displaying in time series, as a pseudo moving image, in-vivo images contained in the in-vivo image group 14a of the subject 1 at a normal display rate. Besides, the display operation icon 112 is a GUI for displaying in time series, as a pseudo moving image, the in-vivo images in the in-vivo image group 14a at a higher display rate than the normal display rate. The display operation icon 113 is a GUI for sequentially displaying in time series, as a still image, each in-vivo image in the in-vivo image group 14a. The display operation icon 114 is a GUI for displaying in a reverse order of the time series, as a pseudo moving image, the in-vivo images in the in-vivo image group 14a at the normal display rate. The display operation icon 115 is a GUI for displaying in the reverse order of the time series, as a pseudo moving image, the in-vivo images in the in-vivo image group 14a at a higher display rate than the normal display rate. The display operation icon 116 is a GUI for sequentially displaying in the reverse order of the time series, as a still image, each in-vivo image in the in-vivo image group 14a. The display operation icon 117 is a GUI for pausing with an in-vivo image in the main display area 101 displayed as a still image.

In the in-vivo images in the in-vivo image group 14a to be operated and displayed by the display operation icons 111 to 117, at least an in-vivo image set as the normal image 120 is contained. Besides, when the display switching area 107 is specified in the main display area 101, each in-vivo image set as the differently-processed image 120a in the display switching area 107 is contained in the in-vivo images in the in-vivo image group 14a.

The input unit 13 has a function as an indication unit which indicates the display switching area 107 of the normal image 120 displayed in the main display area 101. Specifically, the input unit 13 is realized by using inputting devices such as a keyboard and a mouse and inputs various kinds of information to the control unit 15 in response to an inputting operation by a user. More specifically, the input unit 13 inputs various kinds of instruction information for instructing the control unit 15, data for specifying the subject 1, and the like to the control unit 15. As the instruction information input by the input unit 13, area instruction information which indicates coordinates (x, y) of a position P, a size (radius r), and the like of the display switching area 107 to be specified in the main display area 101, display instruction information corresponding to the display operation icon selected from the display operation icons 111 to 117 through a click operation and the like with the pointer 106 set, and the like can be listed.

The storage unit 14 is realized by using recording media such as a random access memory (RAM), an electrically erasable and programmable read-only memory (EEPROM), a hard disk, and the like, stores various kinds of data and the like which the control unit 15 instructs the storage unit 14 to write, and transmits the stored data that the control unit 15 instructs to read out to the control unit 15. Specifically, the storage unit 14 stores the storage data imported by the reader/writer 11 from the recording medium 5, i.e., the in-vivo image group 14a and time data of each in-vivo image of the subject 1 based on the control of the control unit 15. The in-vivo image group 14a includes the white light image group Da and the spectral image group Db, generated by the receiver 3, of the same number. In addition, the storage unit 14 stores the data for specifying the subject 1 or the information such as the size information of the display switching area 107 input by the input unit 13. When instructed by the control unit 15 to read out an in-vivo image whose frame number is n (n is an integer equal to or more than one), the storage unit 14 reads out each image data of the white light image and the spectral image having the same frame number n, respectively from the white light image group Da and the spectral image group Db both groups being as the in-vivo image group 14a, and transmits each of the read image data to the control unit 15.

Here, the white light image group Da and the spectral image group Db which are stored in the storage unit 14 as the in-vivo image group 14a are image groups which include the same number of images and have a coincident positional relationship with respect to the subject between images of the same frame number. Specifically, the white light image of the frame number n in the white light image group Da and the spectral image of the frame number n in the spectral light image group Db are in-vivo images which are generated by the receiver 3 based on color data of an in-vivo image of the frame number n captured by the capsule endoscope 2 and are obtained from the same subject. In other words, the white light image of the frame number n in the white light image group Da and the spectral image of the frame number n in the spectral image group Db have a coincident positional relationship with respect to the subject and are obtained through different image processes, respectively.

The control unit 15 controls operations of the reader/writer 11, the display unit 12, the input unit 13, and the storage unit 14, which constitute the image display apparatus 4, and controls an input and an output of signals among these units. Specifically, the control unit 15 controls the reader/writer 11 to import data stored in the recording medium 5 based on instruction information input by the input unit 13 and controls the storage unit 14 to store the imported storage data (the in-vivo image group 14a, time data of each in-vivo image, and the like). Besides, the control unit 15 controls the reader/writer 11 to store the data for specifying the subject 1 which is input by the input unit 13 in the recording medium 5. Meanwhile, the control unit 15 controls the display unit 12 to display the display window 100 shown in FIG. 3 based on instruction information input by the input unit 13.

In addition, the control unit 15 includes a display controller 15a which controls an image displaying operation of the display unit 12, an image selector 15b which selects an in-vivo image to be displayed as the normal image 120 in the display unit 12 and an in-vivo image to be displayed as the differently-processed image 120a in the display unit 120, and an area setting unit 15c which sets the display switching area 107 described above.

The display controller 15a controls the display unit 12 to display, as a still image or a pseudo moving image, the normal image 120 in the main display area 101 based on display instruction information input by the input unit 13. Specifically, the display controller 15a reads out image data of each of a white light image Da-n and a spectral image Db-n having the same frame number respectively from the white light image group Da and the spectral image group Db in the storage unit 14. The display controller 15a controls the display unit 12 to display image data, from the image data of the white light image Da-n and the image data of the spectral image Db-n, selected by the image selector 15b as the normal image 120 in the main display area 101 as the normal image 120. In this case, the display controller 15a controls the display unit 12 to display the normal image 120 within a predetermined positional range in an orthogonal biaxial coordinate system formed by an X axis and a Y axis set in the main display area 101. The display controller 15a may control the display unit 12 to display the normal image 120 in the main display area 101 and to hide, at the same time, the differently-processed image 120a on a back side of the normal image 120 in a manner in which a positional relationship with respect to the subject between the normal image 120 and the differently-processed image 120a is coincident.

Besides, when the display switching area 107 of the normal image 120 is set in the main display area 101, the display controller 15a arranges the normal image 120 in an image part outside the display switching area 107 of the normal image 120. In addition, the display controller 1Sa controls the display unit 12 to switch, for display, an image part inside the display switching area 107 of the normal image 120 to an image part, having a coincident positional relationship with the inside part of the display switching area 107 with respect to the subject, of the differently-processed image 120a. In this case, the display controller 15a hides the differently-processed image 120a on the back side of the normal image 120 in the manner of having a coincident positional relationship with the normal image 120 with respect to the subject and moves the image part, corresponding to the image part inside the display switching area 107 of the normal image 120, of the differently-processed image 120a from the back side to a front side. Thus, the image part inside the display switching area 107 may be switched from the normal image 120 to the differently-processed image 120*a*. Moreover, the display controller 15*a* cuts an image part, corresponding to the image part inside the display switching area 107, of the normal image 120 and an image part, corresponding to the image part inside the display switching area 107, of the differently-processed image 120*a*, and replaces the cut image parts. Thus, the image part inside the display switching area 107 may be switched from the normal image 120 to the differently-processed image 120*a*. Here in the embodiment, when the normal image 120 is the white light image Da-n, the differently-processed image 120*a* is the spectral image Db-n and when the normal image 120 is the spectral image Db-n, the differently-processed image 120*a* is the white light image Da-n.

The image selector 15*b* selects an in-vivo image to be displayed as the normal image 120 in the display unit 12 and an in-vivo image as the differently-processed image 120*a* in the display unit 12 from the in-vivo image group 14*a* in the storage unit 14 based on the instruction information input by the input unit 13. Specifically, the image selector 15*b* selects, as the normal image 120, one of the white light image group Da and the spectral image group Db which are the in-vivo image group 14*a* and selects, as the differently-processed image 120*a*, the other one.

The area setting unit 15*c* sets the display switching area 107 based on area instruction information input by the input unit 13. Specifically, the area setting unit 15*c* sets an orthogonal biaxial coordinate system formed by an X axis and a Y axis in the main display area 101 as shown in FIG. 3 and defines, by this orthogonal biaxial coordinate system, a coordinate position in the main display area 101. Meanwhile, the area setting unit 15*c* sets the position P of the display switching area 107, the size (radius r) of the display switching area 107, and the like in the main display area 101 based on the area instruction information input by the input unit 13. The area setting unit 15*c* sets the display switching area 107 whose center is the position P indicated by the pointer 106 and whose radius is r in the main display area 101, for example as shown in FIG. 3.

The area setting unit 15*c* can update the position of the display switching area 107 by following a movement of the pointer 106 based on the area instruction information input by the input unit 13. Besides, the area setting unit 15*c* can also fix the display switching area 107 at a desired position in the main display area 101 irrespective of the movement of the pointer 106. Furthermore, the area setting unit 15*c* can update the radius r of the display switching area 107 based on the area instruction information input by the input unit 13.

Figure 4:
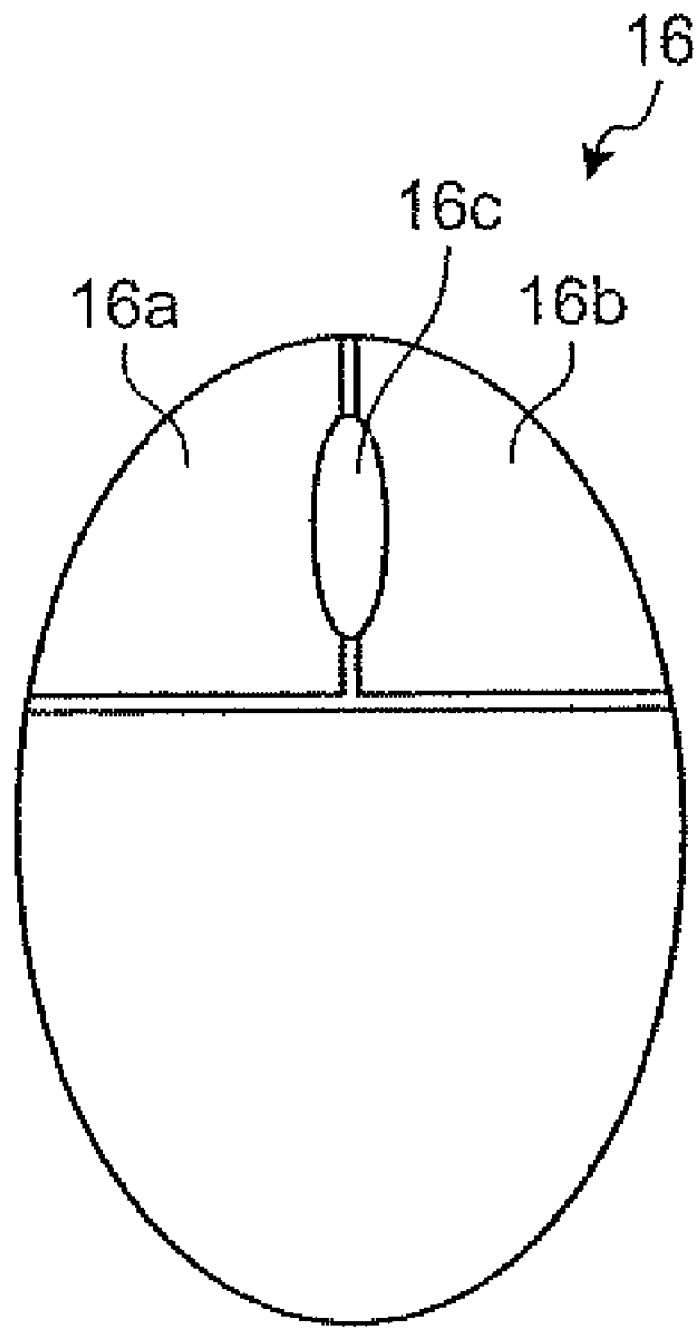
FIG. 4 is a view illustrating an operational specification in an input unit in switching an image part inside a display switching area in the embodiment of the present invention.
Figure 5:
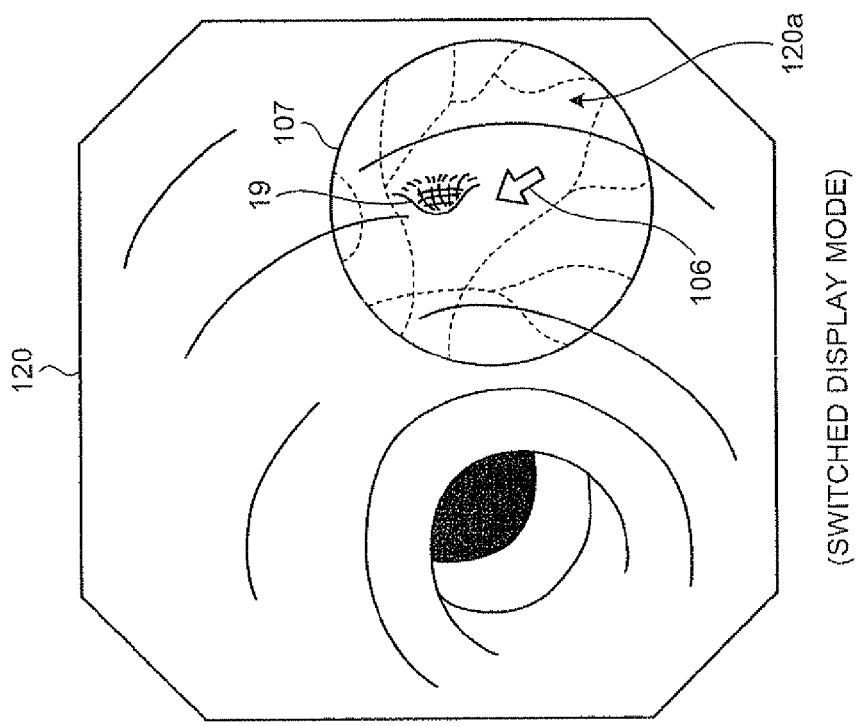
FIG. 5 is a view of a state in which the image part inside the display switching area is switched from a normal image to a differently-processed image in the embodiment of the present invention.
Figure 5:
Figure 5:
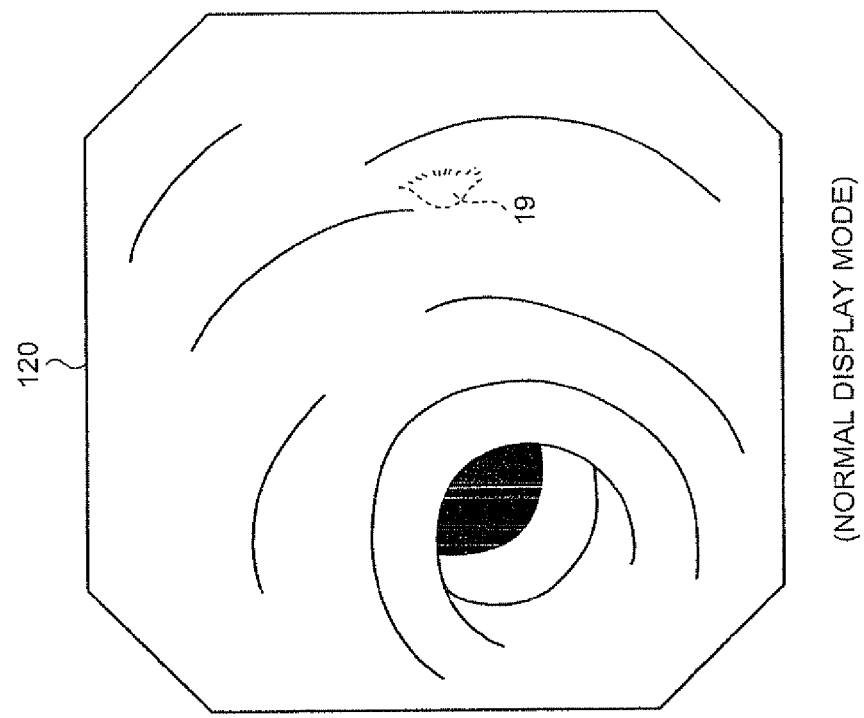

Next, an operation of the image display apparatus 4 in switching and displaying the image part inside the display switching area 107 will be explained with an example of a case where the white light image group Da is selected as the normal image 120 and the spectral image group Db is selected as the differently-processed image 120*a* in the in-vivo image group 14*a* of the subject 1. FIG. 4 is a view illustrating an operational specification in the input unit in switching the image part inside the display switching area. FIG. 5 is a view of a state in which the image part inside the display switching area is switched from the normal image to the differently-processed image. In FIG. 4, a mouse 16 as a part of the input unit 13 is illustrated. The operation of the image display apparatus 4 in switching the image part inside the display switching area 107 from the normal image 120 to the differently-processed image 120*a* will be explained below with reference to FIGS. 2, 3, 4, and 5.

The image display apparatus 4 displays, as a pseudo moving image or a still image, the normal image 120 in the main display area 101 of the display unit 12 in response to the inputting operation of the input unit 13. In the image display apparatus 4, the image selector 15*b* selects each white light image in the white light image group Da as the normal image 120 and selects each spectral image in the spectral image group Db as the differently-processed image 120*a* from the in-vivo image group 14*a* in the storage unit 14. The display controller 15*a* continuously or intermittently reads out the white light image Da-n and the spectral image Db-n having the same frame number sequentially from the white light image group Da and the spectral image group Db in the storage unit 14, respectively. Besides, the display controller 15*a* controls the display unit 12 to display continuously the read white light image Da-n as the normal image 120 in the main display area 101 (in other words, to display as a pseudo moving image) or to display as a still image.

A user such as a doctor and a nurse sequentially observes the normal image 120 displayed as a pseudo moving image or a still image in the main display area 101 of the display unit 12, i.e., the white light image Da-n and observes the inside of organs of the subject 1 through the observation of the white light image Da-n. The user visually recognizes whether or not there is an area of interest which needs to be paid attention to in the examination of the inside of organs in the white light image Da-n sequentially displayed in this manner. Such area of interest has a possibility of including a pathognomonic site such as a lesion site and a bleeding site in the inside of organs.

Here, when the user finds out such an area of interest in the white light image Da-n, the user operates the input unit 13 of the image display apparatus 4 to switch an image part corresponding to the area of interest in the white light image Da-n to spectral image data. In the image display apparatus 4, the input unit 13 inputs area instruction information which indicates the positional coordinates or the size, to be specified in the main display area 101, of the display switching area 107 to the control unit 15 in response to the inputting operation by the user. The control unit 15 sets the display switching area 107 in the main display area 101 based on the area instruction information.

Specifically, the mouse 16 as a part of the input unit 13 inputs, in response to a mouse operation of moving the pointer 106 to the main display area 101, information indicating coordinates (x, y) of the position P indicated by the pointer 106. The information of the coordinates of the position P is input to the control unit 15 as area instruction information which indicates the position of the display switching area 107 in the main display area 101. The area setting unit 15*c* sets the display switching area 107 whose center is the position P and whose radius is r in the main display area 101 based on the area instruction information. When the mouse operation of moving the pointer 106 is performed, the mouse 16 inputs to the control unit 15 the information of the coordinates of the position P which changes by following the movement of the pointer 106 as the area instruction information. The area setting unit 15*c* follows the movement of the pointer 106 and updates the position P of the display switching area 107.

Here, when a single click operation of clicking a right button 16*b* shown in FIG. 4 is performed once, the mouse 16 inputs area instruction information which fixes the position P of the display switching area 107 to the control unit 15. The area setting unit 15*c* fixes the position P of the display switching area 107 at the time when the right button 16*b* of the mouse 16 is once clicked based on the area instruction information. In this case, the area setting unit 15*c* maintains the fixed state of the position P of the display switching area 107 even when the pointer 106 is moved in response to the operation of the mouse 16. Then, when the single click operation of the right button 16b is again performed, the mouse 16 inputs area instruction information which releases the fixed state of the position P of the display switching area 107 to the control unit 15. The area setting unit 15c releases the fixed state of the position P of the display switching area 107 based on the area instruction information and then updates the position P of the display switching area 107 by following the movement of the pointer 106 as described above.

On the other hand, when a drag operation is performed at a state where a left button 16a shown in FIG. 4 is kept depressed, the mouse 16 inputs area instruction information of indicating the radius r of the display switching area 107 to the control unit 15. The area setting unit 15c updates the radius r of the display switching area 107 based on the area instruction information according to the drag operation of the mouse 16. In this case, the area setting unit 15c determines an increase or a decrease of the radius r in response to a direction of the movement of the drag operation of the mouse 16 and determines an amount of change of the radius r according to the movement amount of the drag operation.

In the state where the position P and the radius r of the display switching area 107 are set, the display controller 15a displays, as an image part outside the display switching area 107 in the normal image 120, an image part, corresponding to the outside of the display switching area 107, of the white light image Da-n. In addition, the display controller 15a controls the display unit 12 to display an image part, corresponding to the inside of the display switching area 107, of the spectral image Db-n as an image part, corresponding to the image area inside the display switching area 107, of the differently-processed image 120a. In this case, the display controller 15a hides the spectral image Db-n as the differently-processed image 120a on the back side of the white light image Da-n as the normal image 120, for example, in a manner of having a coincident positional relationship with the white light image Da-n with respect to the subject and moves the image part, corresponding to the image part inside the display switching area 107, of the spectral image Db-n from the back side to a front side of the white light image Da-n. Thus, the image part inside the display switching area 107 is changed over from the white light image Da-n to the spectral image Db-n with the state of having a coincident positional relationship with respect to the subject maintained.

Here, the display controller 15a cuts an image part, corresponding to the image part inside the display switching area 107, of the white light image Da-n and an image part, corresponding to the image part inside the display switching area 107, of the spectral image Db-n and replaces the cut image parts. Thus, the image part inside the display switching area 107 may be changed over from the white light image Da-n to the spectral image Db-n with the state of having a coincident positional relationship with respect to the subject maintained.

Here, the mouse 16 shown in FIG. 4 inputs to the control unit 15 instruction information of increasing or decreasing a frame number of the normal image 120 in the main display area 101 in response to an operation of a wheel button 16c. The display controller 15a controls the display unit 12 to switch the white light image Da-n currently displayed as the normal image 120 in the main display area 101 sequentially to a white light image having a smaller frame number (n−1, n−2, . . . ) or a white light image having a larger frame number (n+1, n+2, . . . ) and display the switched white light image based on the instruction information in response to the operation of the wheel button 16c. Besides, when the display switching area 107 is set in the white light image Da-n in the main display area 101, the display controller 15a controls the display unit 12 to switch the spectral image Db-n as the image part inside the display switching area 107 sequentially to a spectral image having a smaller frame number (n−1, n−2, . . . ) or a spectral image having a larger frame number (n+1, n+2, . . . ) and display the switched spectral image in accordance with the switching in the display of the white light image based on the instruction information in response to the operation of the wheel button 16c.

When the display switching area 107 is set in white light images which are sequentially displayed as a moving image as the normal image 120 in the main display area 101, the display controller 15a controls the display unit 12 to sequentially switch and display the image part inside the display switching area 107 and the image part outside the display switching area 107 similarly to the switching in the display of the white light image and the spectral image based on the instruction information in response to the operation of the wheel button 16c.

Based on the control of the display controller 15a, the display unit 12 switches, for display, an area of user's interest in an in-vivo image displayed as the normal image 120 in the main display area 101 to the differently-processed image 120a which has a coincident positional relationship with the normal image 120 with respect to the subject. Specifically, the display switching area 107 is set in an image part including a lesion site 19 in the normal image 120 displayed as a white light image, i.e., in an area of user's interest at which the pointer 106 is located as shown in FIG. 5. The display unit 12 switches, for display, the image part inside the display switching area 107 from a white light image which is useful for a normal observation of in-vivo images to a spectral image which allows visually and easily recognizing a state of the inside of organs such as the lesion site 19 as a part having a convex/concave shape in body tissues. In this case, the display unit 12 changes over from a white light image to a spectral image in a state of keeping the positional relationship of the lesion site 19 in the image part inside the display switching area 107 coincident. As a result of this, the display unit 12 can switch the image part of the white light image capturing the lesion site 19 to the spectral image which can depict the state of the inside of organs such as a capillary blood vessel in a superficial layer of a mucus membrane, a deep blood vessel, and a concave/convex part of body tissues with the positional relationship in this image part with respect to the subject maintained.

Figure 6:
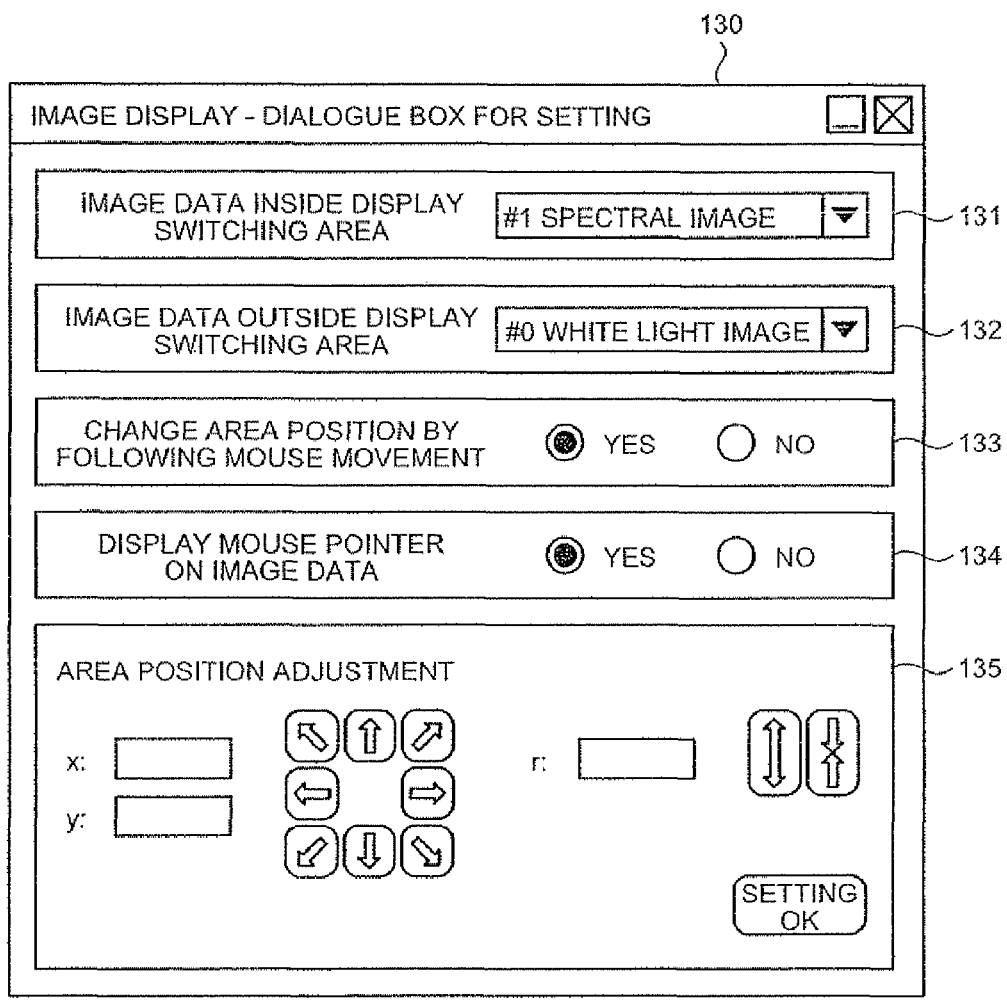
FIG. 6 is a view of a specific example of a setting window for performing an image display setting in the embodiment of the present invention.

Next, an image display setting of the image display apparatus 4 according to the present invention will be explained. FIG. 6 is a view of a specific example of a setting window for performing an image display setting. In the image display apparatus 4 according to the present invention, the control unit 15 controls the display unit 12 to display a setting window 130 illustrated in FIG. 6 as an example when instruction information corresponding to the image display setting icon shown in FIG. 3 is input by the input unit 13.

The setting window 130 includes an inside area image setting box 131, an outside area image setting box 132, an area shift setting box 133, a pointer display setting box 134, and an area setting box 135 as shown in FIG. 6. The inside area image setting box 131 sets image data to be displayed as an image part inside the display switching area 107. The outside area image setting box 132 sets image data to be displayed as an image part outside the display switching area 107. The area shift setting box 133 sets an availability of shifting the display switching area 107. The pointer display setting box 134 sets whether or not to display the pointer 106. The area setting box 135 sets the position and the size of the display switching area 107.

The inside area image setting box 131 is a GUI for setting image data of the differently-processed image 120a in switching the image part inside the display switching area 107 from the normal image 120 to the differently-processed image 120a. Specifically, the inside area image setting box 131 displays a drop-down list of selection target image data (a white light image, a spectral image, and the like, for example) in response to the click operation and the like of the input unit 13. The input unit 13 inputs instruction information of image data selected as the differently-processed image 120a from the drop-down list in the inside area image setting box 131 to the control unit 15. In this case, the image selector 15b selects image data (the spectral image group Db in the state shown in FIG. 6) as the differently-processed image 120a from the in-vivo image group 14a in the storage unit 14 based on the instruction information of the selection. As a result of this, the image data selected by the image selector 15b is set as the image data of the differently-processed image 120a.

The outside area image setting box 132 is a GUI for setting image data of the normal image 120 to be displayed as an image part outside the display switching area 107. Specifically, the outside area image setting box 132 displays a drop-down list of selection target image data (a white light image, a spectral image, and the like, for example) in response to the click operation and the like of the input unit 13. The input unit 13 inputs instruction information of image data selected as the normal image 120 from the drop-down list in the outside area image setting box 132 to the control unit 15. In this case, the image selector 15b selects image data (the white light image group Da in the state shown in FIG. 6) as the normal image 120 from the in-vivo image group 14a in the storage unit 14 based on the instruction information of the selection. As a result of this, the image data selected by the image selector 15b is set as the image data of the normal image 120.

The area shift setting box 133 is a GUI for setting whether or not to shift the display switching area 107 set in the main display area 101 by following the movement of the pointer 106. Specifically, the area shift setting box 133 has two checkboxes for selecting whether or not to change the position of the display switching area 107 by following the movement of the pointer 106 as shown in FIG. 6. The input unit 13 inputs instruction information corresponding to one of the two checkboxes to the control unit 15. Here, when the input unit 13 inputs instruction information corresponding to one checkbox for "changing the area position", the control unit 15 allows a change in the position of the display switching area 107 by following the movement of the pointer 106. In this case, the area setting unit 15c sequentially updates the position of the display switching area 107 by following the movement of the pointer 106 as described above. On the other hand, when the input unit 13 inputs instruction information corresponding to the other checkbox for "not changing the area position", the control unit 15 does not allow the change in the position of the display switching area 107 by following the movement of the pointer 106. In this case, the area setting unit 15c fixes the position of the display switching area 107 irrespective of the movement of the pointer 106.

The pointer display setting box 134 is a GUI for setting whether or not to display, on image data, the pointer 106 as a form of indicating the display switching area 107 in the main display area 101 as shown in FIG. 3. Specifically, the pointer display setting box 134 has two checkboxes for selecting whether or not to display the pointer 106 as shown in FIG. 6. The input unit 13 inputs instruction information corresponding to one of the two checkboxes to the control unit 15. Here, when the input unit 13 inputs instruction information corresponding to one checkbox for "displaying the mouse pointer", the display controller 15a controls the display unit 12 to display the pointer 106 even when the pointer 106 is located on the image data (the normal image 120 or the differently-processed image 120a) in the main display area 101. On the other hand, when the input unit 13 inputs instruction information corresponding to the other checkbox for "not displaying the mouse pointer", the display controller 15a controls the display unit 12 not to display the pointer 106 located on the image data in the main display area 101.

The area setting box 135 is a GUI for setting the position and the size of the display switching area 107 in the main display area 101. Specifically, the area setting box 135 has input boxes for inputting positional coordinates of the display switching area 107 and position adjustment buttons as shown in FIG. 6. The input unit 13 inputs to the control unit 15 positional coordinates corresponding to positional coordinates input through a keystroke in the input boxes or positional coordinates corresponding to a selected positional adjustment button as area instruction information which indicates the position of the display switching area 107. In this case, the area setting unit 15c sets the position P indicated by the area instruction information in the main display area 101 as a position of the display switching area 107.

Besides, the area setting box 135 has an input box for inputting the size (radius r) of the display switching area 107 and a size adjustment buttons for increasing or decreasing the radius r as shown in FIG. 6. The input unit 13 inputs to the control unit 15 a value of the radius r which is input through a keystroke in the input box or a value of the radius r which is increased or decreased according to a selected size adjustment button as area instruction information which indicates the size of the display switching area 107. In this case, the area setting unit 15c sets the radius r indicated by the area instruction information as a size of the display switching area 107.

Figure 7:
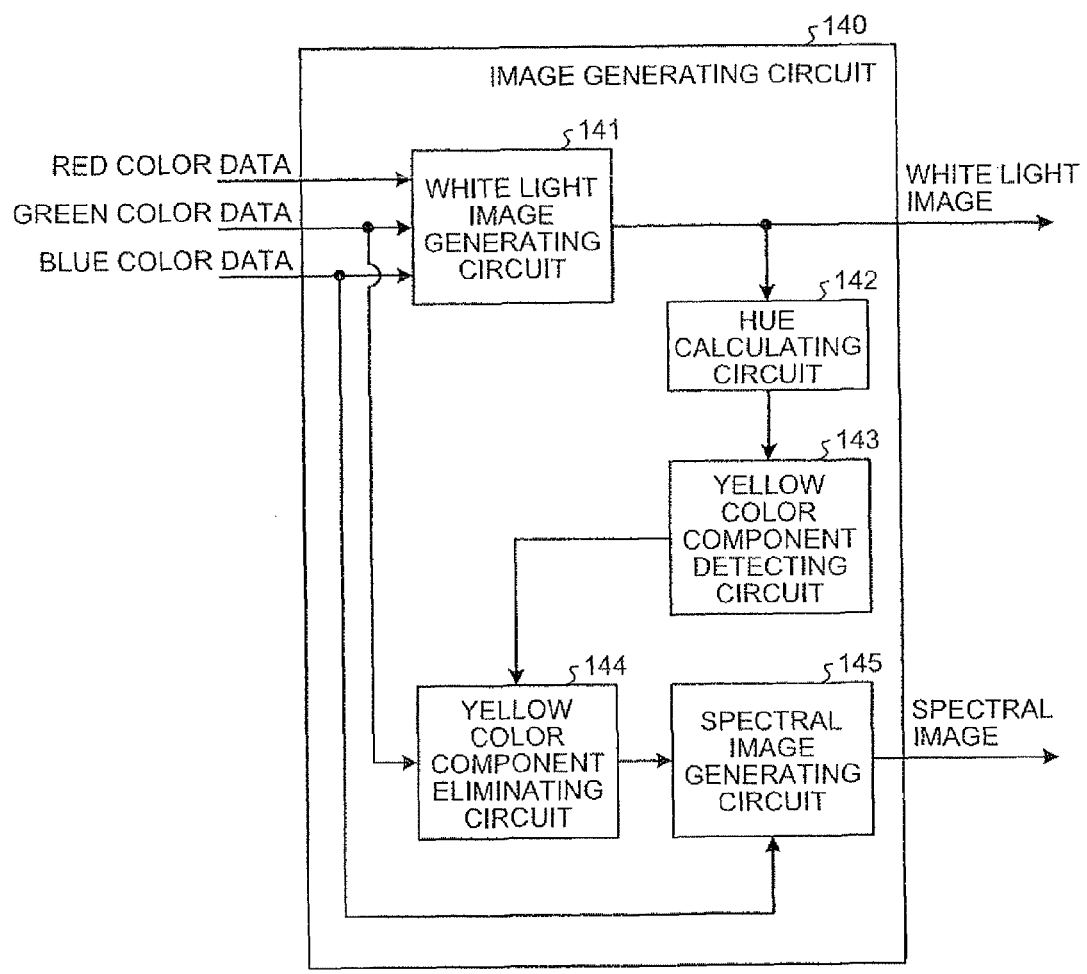
FIG. 7 is a block diagram schematically showing an example of a structure of an image generating circuit integrated in a receiver according to the embodiment of the present invention.

Next, an image generating function of the receiver 3 will be explained. FIG. 7 is a block diagram schematically showing an example of a structure of an image generator (image generating circuit) integrated in the receiver. The receiver 3 shown in FIG. 1 includes an image generating circuit 140 shown in FIG. 7 as an image generating function which allows generating two kinds of images whose positional relationship with respect to the subject is coincident via different image processes respectively. The image generating circuit 140 performs a different image process based on color data of an in-vivo image for one frame obtained from the capsule endoscope 2 and generates two kinds of images, a white light image and a spectral image for example, which have a coincident positional relationship with respect to the subject and obtained respectively via different image processes.

Specifically, the image generating circuit 140 includes a white light image generating circuit 141, a hue calculating circuit 142, a yellow color component detecting circuit 143, a yellow color component eliminating circuit 144, and a spectral image generating circuit 145 as shown in FIG. 7. The white light image generating circuit 141 generates a white light image based on color data of one frame in-vivo image. The hue calculating circuit 142 calculates a hue based on image data of the white light image. The yellow color component detecting circuit 143 detects a yellow color component of the white light image. The yellow color component eliminating circuit 144 eliminates a yellow color component from the color data of the one frame in-vivo image. The spectral image generating circuit 145 generates a spectral image which has a coincident positional relationship with the white light image with respect to the subject.

The white light image generating circuit 141 obtains red color data, green color data, and blue color data as color data of the one frame in-vivo image obtained from the capsule endoscope 2. The white light image generating circuit 141 generates a white light image (color image) as an in-vivo image captured by the capsule endoscope 2 based on the red color data, the green color data, and the blue color data. The image data of the white light image generated by the white light image generating circuit 141 is input to the hue calculating circuit 142, output from the image generating circuit 140, and stored in the recording medium 5 in the receiver 3.

The hue calculating circuit 142 calculates a hue of the white light image based on the image data of the white light image generated by the white light image generating circuit 141. The hue calculating circuit 142 inputs a result of the hue calculation to the yellow color component detecting circuit 143. The yellow color component detecting circuit 143 obtains the result of the hue calculation by the hue calculating circuit 142. Besides, the yellow color component detecting circuit 143 detects a yellow color component of the white light image based on the obtained result of the hue calculation, i.e., based on the hue calculation value of the white light image generated by the white light image generating circuit 141. The yellow color component detecting circuit 143 inputs the detection result of the yellow color component to the yellow color component eliminating circuit 144.

The yellow color component eliminating circuit 144 is for eliminating a yellow color component from green color data among color data of the one frame in-vivo image from the capsule endoscope 2. Specifically, the yellow color component eliminating circuit 144 obtains green color data among color data constituting the same in-vivo image used in the white light image generating circuit 141 and the result of the yellow color component detection by the yellow color component detecting circuit 143. The yellow color component eliminating circuit 144 eliminates a yellow color component from the green color data based on the obtained result of the yellow color component detection and inputs green data after the elimination of the yellow color component to the spectral image generating circuit 145.

The spectral image generating circuit 145 generates an in-vivo image which has a coincident positional relationship with respect to the subject with the white light image generated by the white light image generating circuit 141 through a different image process. Specifically, the spectral image generating circuit 145 obtains the blue color data and the green color data among the color data constituting the same in-vivo image used in the white light image generating circuit 141. In this case, the spectral image generating circuit 145 obtains the green color data via the yellow color component eliminating circuit 144 described above. In other words, the green color data input to the spectral image generating circuit 145 is green color data from which a yellow color component is eliminated by the yellow color component eliminating circuit 144. The spectral image generating circuit 145 combines the green color data obtained in this manner and the blue color data to generate a spectral image. In this case, the spectral image generating circuit 145 uses, as color data of a blue color pixel and a green color pixel, the blue color data whose absorbance level in a blood is high and reflection light level from an inner wall of organs is low and thereby amplifies the blue color data. Besides, the spectral image generating circuit 145 uses the green color data after the elimination of the yellow color component as color data of a red color pixel. The spectral image generating circuit 145 combines the blue color data and the green color data in this manner to generate a spectral image whose positional relationship with respect to the subject is coincident with the white light image generated by the white light image generating circuit 141.

The spectral image generated by the spectral image generating circuit 145 can emphatically depict a state of the inside of organs such as a capillary blood vessel in a superficial layer of a mucus membrane, a deep blood vessel, and a concave/convex part like a lesion site and the like of body tissues, which cannot be easily recognized visually in a white light image. The image data of the spectral image is output from the image generating circuit 140 and stored in the recording medium 5 in the receiver 3 as a spectral image having the same frame number as the white light image generated by the white light image generating circuit 141.

As described above, two kinds of in-vivo images generated by different image processes based on color data of the same in-vivo image are, i.e., an in-vivo image group which includes a first in-vivo image and a second in-vivo image of the same number which have a coincident positional relationship with respect to the subject and are obtained respectively through different image processes is obtained in the embodiment of the present invention. Besides, the first in-vivo image in the in-vivo image group is displayed in the main display area of the display unit as the normal image. When the display switching area of the normal image is specified in the main display area, the first in-vivo image is kept arranged in an image part outside the display switching area in the normal image currently displayed, and an image part inside the display switching area is switched, for display, to an image part, having a coincident positional relationship with the first in-vivo image with respect to the subject, of the second in-vivo image. With such a structure, an area of interest in the first in-vivo image displayed in the display unit can be displayed with the switched image part, having a coincident positional relationship with respect to the subject in the area of interest, of the second in-vivo image in the embodiment. As a result of this, it is possible to realize: an image display apparatus which enables, without missing a pathognomonic site in an area of interest, comparing the area of interest in an in-vivo image in observation with a switched in-vivo image obtained through a different image process; an endoscope system using the same; and an image display method.

In the image display apparatus, the endoscope system using the same, and the image display method according to the embodiment, a user such as a doctor and a nurse can arbitrarily repeat setting and unsetting the display switching area with respect to an area of interest via an operation of the input unit while visually recognizing the area of interest in an in-vivo image in observation. By this, the user can compare the area of interest by an in-vivo image obtained through a different image process without changing a point of view from the area of interest and thereby an observation efficiency of an in-vivo image can be improved.

In addition, image data is generated by arbitrarily combining, through a different image process, color data of an in-vivo image for one frame captured by an endoscope device, i.e., red color data, blue color data, and green color data in the embodiment of the present invention. Therefore, two kinds of in-vivo images which have a coincident positional relationship with the one frame in-vivo image, i.e., an original image with respect to the subject and are obtained respectively through different image processes can be generated for each original image. As a result of this, a set of in-vivo images which have a coincident positional relationship with respect to the subject and are obtained respectively through different image processes can be easily obtained, the in-vivo images being, for example, a white light image as a color in-vivo image which is useful for a normal image observation and a spectral image which is useful for an observation of a state of the inside of organs such as a capillary blood vessel in a superficial layer of a mucus membrane, a deep blood vessel, and a concave/convex part like a lesion site and the like of body tissues, which cannot be easily recognized visually in the white light image.

Moreover, since the position of the display switching area of the normal image is configured to be updated by following the movement of the mouse pointer displayed in the display unit, the mouse pointer is made to move to an area of interest in an in-vivo image in observation in the embodiment of the present invention. By this, the area of interest can be easily switched to an in-vivo image obtained through a different image process. In addition, the area of interest can be easily returned to the normal image before the display switching by putting the mouse pointer out of the area of interest. By this, the user can easily compare the area of interest by the in-vivo image obtained through a different image process and thereby an observation efficiency of an in-vivo image can be improved further.

Furthermore, when the mouse pointer is located on the in-vivo image in observation displayed in the display unit, the area of interest in the display switching area can be observed without being aware of the presence of the mouse pointer since the mouse pointer on the in-vivo image can be changed to be hidden in the embodiment of the present invention.

Besides, the position of the display switching area can be fixed irrespective of the movement of the mouse pointer in the embodiment of the present invention. Therefore, the mouse pointer can be moved without changing the position of the display switching area after setting the display switching area on the in-vivo image in observation. By this, an operation of displaying an in-vivo image or other various operations including a size change of the display switching area and the like of the input unit (specifically, the mouse) can be performed while maintaining a fixed state of the position of the display switching area at the area of interest in the in-vivo image.

It should be noted that, the number of in-vivo images to be displayed at the same time in the main display area 101 of the display unit 12 as the normal image is configured to be one as shown in FIG. 3 in the embodiment described above, however, the present invention is not limited to this and the number of in-vivo images to be displayed at the same time in the main display area 101 as the normal image may be more than one. In this case, the display switching area 107 may be set for each of a plurality of in-vivo images in the main display area 101 or may be set for at least one of the plurality of in-vivo images.

Figure 8:
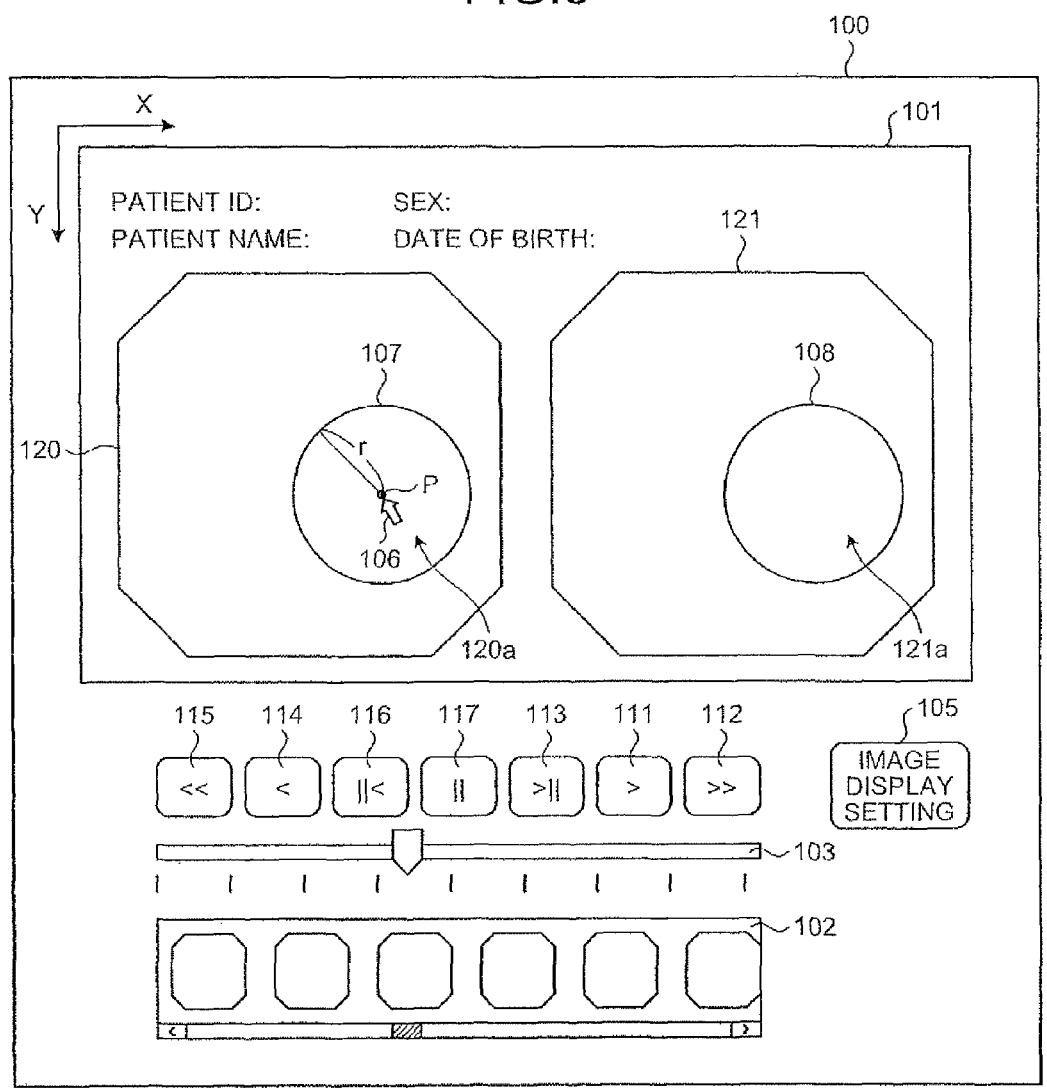
FIG. 8 is a view of a specific example of a display window in a case of displaying in-vivo images for two frames at the same time in the embodiment of the present invention.

FIG. 8 is a view of a specific example of a display window in a case of displaying in-vivo images for two frames at the same time. The display unit 12 displays two-frame normal images 120 and 121 in the main display area 101 at the same time as shown in FIG. 8. In this case, the display controller 15a reads out the two-frame normal images 120 and 121 (white light images whose frame numbers are respectively n and n+1, for example) and two-frame differently-processed images 120a and 121a (spectral images whose frame numbers are respectively n and n+1, for example) from the in-vivo image group 14a in the storage unit 14. Besides, the display controller 15a controls the display unit 12 to display the read normal images 120 and 121 in the main display area 101. Here, when the area setting unit 15c sets display switching areas 107 and 108 respectively for the normal images 120 and 121, the display controller 15a switches an image part inside the display switching area 107 from the normal image 120 to the differently-processed image 120a. In addition to this, the display controller 15a controls the display unit 12 to switch an image part inside the display switching area 108 from the normal image 121 to the differently-processed image 121a. The display switching areas 107 and 108 may be set at the same image parts respectively in the normal images 120 and 121, may be mutually linked and shifted, or may be changed in size.

Furthermore, a list (an index) of a plurality of in-vivo images may be displayed in the main display area 101 of the display unit 12. FIG. 9 is a view of a specific example of a display window in a case of displaying a plurality of in-vivo images with index. The display unit 12 displays a list of normal image 122 which is a group of in-vivo images arranged in a matrix state in the main display area 101 as shown in FIG. 9. Each image of the normal image 122 is a reduced-size image of an original in-vivo image. The display controller 15a reads out plural pieces of first image data (a plurality of white light images, for example) to be displayed in a list as the normal image 122 and plural pieces of second image data (a plurality of spectral images, for example) which have the same frame numbers respectively with the plural pieces of first image data and are obtained through different image processes from the in-vivo image group 14a in the storage unit 14. Besides, the display controller 15a controls the display unit 12 to display a list of the read plural pieces of first image data in the main display area 101.

Here, the area setting unit 15c divides the main display area 101 in a matrix state corresponding to a display position of each image displayed in a list as the normal image 122 and treats each of the divided multiple areas in the main display area 101 as a fixed area which can be alternatively set as the display switching area of the normal image 122. The input unit 13 is used to set the pointer 106 on an image of the normal image 122 displayed in a list in the main display area 101 and perform a click operation and the like. By this, area instruction information which indicates a divided area at a position indicated by the pointer 106 as the display switching area is input to the control unit 15. The area setting unit 15c sets the divided area where the pointer 106 is located among the multiple divided areas in the main display area 101 as the display switching area based on the area instruction information.

The display controller 15a controls the display unit 12 to switch, for display, an image (first image data) inside the divided area which is set as the display switching area by the area setting unit 15c to a differently-processed image 122a (second image data) which has a coincident positional relationship with the image inside the display switching area with respect to the subject and are obtained through a different image process as shown in FIG. 9. At the same time, the display controller 15a keeps each of the plural pieces of first image data arranged in each image area outside the display switching area (the divided area where the pointer 106 is located) among the plurality of images displayed in a list as the normal image 122 in the main display area 101.

Meanwhile, the white light image Da-n is displayed as the normal image 120 in the main display area 101 in the embodiment described above. Here, when the display switching area 107 is set on the white light image Da-n, the image part inside the display switching area 107 is switched from the white light image Da-n to the spectral image Db-n in the embodiment. However, the present invention is not limited to this and each setting can be changed in the inside area image setting box 131 and the outside area image setting box 132 of the setting window 130 shown in FIG. 6. By this, the spectral image Db-n is displayed in the main display area 101 as the normal image 120. Besides, when the display switching area 107 is set on the spectral image Db-n, the image part inside the display switching area 107 can be switched from the spectral image Db-n to the white light image Da-n.

In addition, a white light image and a spectral image are taken as examples of image data, selected as the normal image 120 and the differently-processed image 120a, in the in-vivo image group 14a in the embodiment. However, the present invention is not limited to this and image data in the in-vivo image group 14a may be a weighted image whose predetermined color such as a red color is weighted or may be a monochrome image.

Moreover, the image generating circuit 140 which generates two kinds of in-vivo images which have a coincident positional relationship with respect to the subject and are obtained respectively through different image processes is integrated in the receiver 3 in the embodiment described above. However, the present invention is not limited to this and the image generating circuit 140 may be integrated in the image display apparatus 4 according to the present invention. In this case, the receiver 3 stores the in-vivo image group 14a received from the capsule endoscope 2 in the recording medium 5. The image display apparatus 4 uses the reader/writer 11 to import the in-vivo image group 14a from the recording medium 5 and uses the image generating circuit 140 to generate the white light image group Da and the spectral image group Db based on color data of each in-vivo image in the imported in-vivo image group 14a.

Besides, the capsule endoscope 2 of a swallowable type is taken as an example of an endoscope device which captures in-vivo images of the subject 1 in the embodiment described above. However, the present invention is not limited to this and the endoscope device which captures in-vivo images of the subject 1 may be an endoscope of an insertion type which is provided with an imaging function at a head of an insertion unit which is inserted into an inside of organs of the subject 1 and has an elongated shape. In an endoscope system including such an endoscope of an insertion type and the image display apparatus 4, the image display apparatus 4 displays the in-vivo images of the subject 1 captured by the imaging unit of the endoscope in real time. In this case, the image display apparatus 4 uses the image generating circuit 140 to generate the white light image group Da and the spectral image group Db based on color data of one frame in-vivo image captured by the imaging unit of the endoscope. In addition, the image display apparatus 4 displays each image data of the white light image group Da and the spectral image group Db respectively as the normal image 120 and the differently-processed image 120a, similarly to the case of the in-vivo image group 14a captured by the capsule endoscope 2.

In addition, each image data of the in-vivo image group 14a obtained via the recording medium 5 is displayed on the display unit 12 in the embodiment. However, the present invention is not limited to this and the image display apparatus 4 according to the present invention may include a receiver which receives an image signal from the capsule endoscope 2 and the image generating circuit 140 which generates the white light image group Da and the spectral image group Db based on color data of an in-vivo image received by the receiver, and may display the in-vivo image captured by the capsule endoscope 2 inside the subject I in real time.

Moreover, though the display switching area 107 having a circular shape is taken as an example in the embodiment described above, the display switching area of the image display apparatus according to the present invention is not limited to that having a circular shape and may be any other desired shapes including a rectangular shape, an oval shape, and the like.

Furthermore, the display operation icons 111 to 117 which are set in advance in the display window 100 are used to perform an operation of displaying the normal image 120 as a moving image or an operation of displaying the normal image 120 as a still image in the embodiment. However, the present invention is not limited to this, and a group of display operation icons similar to the display operation icons 111 to 117 may be additionally displayed in the neighborhood of the pointer 106 in response to the operation of the mouse 16 and the additionally-displayed group of display operation icons may be used to perform the operation of displaying the normal image 120 as a moving image or the operation of displaying the normal image 120 as a still image. In this case, the group of display operation icons may be additionally displayed in response to a double click operation and the like of the right button 16b of the mouse 16, or may be additionally displayed in response to a single click operation, a double click operation, and the like of the left button 16a.

As described above, in the image display apparatus, the endoscope system using the same, and the image display method according to the embodiment, a display unit displays, among an image group including a first image and a second image of the same number which have a coincident positional relationship with respect to a subject and are obtained respectively through different image processes, at least the first image in a display area, an indication unit indicates a display switching area in the first image displayed in the display area, a control unit controls the display unit to keep the first image arranged in an image part outside the display switching area and to switch an image part inside the display switching area of the first image to an image part, having a coincident positional relationship with the image part inside the display switching area of the first image with respect to the subject, of the second image. Thus, an area of interest in the first image can be displayed by switching to the image part, having a coincident positional relationship with respect to the subject in the area of interest, of the second image, which allows the present invention to be advantageous in that an area of interest in an in-vivo image in observation can be compared with a switched in-vivo image obtained through a different image process without missing a pathognomonic site in the area of interest.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus, comprising:
   a storage unit which stores an image group including a same number of first and second images which have a coincident positional relationship with respect to a subject and are respectively obtained through different image processes;
   a display unit which displays at least the first image in a display area;
   an input unit which indicates a display switching area of the first image displayed in the display area; and
   a controller which controls the display unit to keep displaying the first image in an image part outside the display switching area and to switch an image part inside the display switching area of the first image to an image part, having a coincident positional relationship with the image part inside the display switching area of the first image with respect to the subject, of the second image.

2. The image display apparatus according to claim 1, wherein
the input unit inputs at least positional information of the display switching area, and
the controller controls the display unit to display a pointer at a position in the display area specified by the positional information.

3. The image display apparatus according to claim 2, wherein
the display unit moves a display position of the pointer in response to the positional information, and
the controller moves the display switching area by following the display position of the pointer.

4. The image display apparatus according to claim 1, wherein
the display unit displays a plurality of first images in the display area,
the input unit indicates display switching areas of the plurality of first images respectively, and
the controller controls the display unit to keep displaying the plurality of first images in image parts outside the display switching areas respectively and to switch image parts inside the display switching areas of the plurality of first images to image parts, having coincident positional relationships with image parts inside the display switching areas of the plurality of first images with respect to the subject, of a plurality of second images, respectively.

5. The image display apparatus according to claim 1, wherein
the first image is a multiple-image group,
the display unit displays a list of the first image as the multiple-image group in the display area, and
the controller controls the display unit to keep displaying the first image outside the display switching area among the multiple-image group and to switch an image inside the display switching area to the second image having a coincident positional relationship with the image inside the display switching area with respect to the subject.

6. The image display apparatus according to claim 5, wherein
the input unit selectively indicates the display switching area among multiple areas which are created by dividing the display area in accordance with a display array of the multiple-image group, and
the controller controls the display unit to keep displaying the first image outside the display switching area indicated among the multiple divided areas by the input unit and to switch the image inside the display switching area to the second image having a coincident positional relationship with the image inside the display switching area with respect to the subject.

7. The image display apparatus according to claim 1, wherein the first image and the second image capture a same subject and are generated respectively through different image processes based on color data of a same image.

8. The image display apparatus according to claim 7, wherein the same image is an in-vivo image captured by a capsule endoscope which is inserted into an inside of an organ of the subject.

9. An endoscope system, comprising the image display apparatus according to claim 1.

10. An endoscope system, comprising:
an endoscope device which captures an in-vivo image of a subject;
an image generator which generates a first image and a second image which have a coincident positional relationship with respect to the subject and are respectively obtained through different image processes based on color data of one frame in-vivo image captured by the endoscope device;
a display unit which displays at least the first image in a display area;
an input unit which indicates a display switching area of the first image displayed in the display area; and
a controller which controls the display unit to keep displaying the first image in an image part outside the display switching area and to switch an image part inside the display switching area of the first image to an image part, having a coincident positional relationship with the image part inside the display switching area of the first image with respect to the subject, of the second image.

11. The endoscope system according to claim 10, wherein the display unit displays at least the first image in real time.

12. The endoscope system according to claim 10, wherein the endoscope device is a capsule endoscope.

13. The endoscope system according to claim 10, wherein
the first image is a white light image generated by combining red color data, green color data, and blue color data obtained by illuminating with a white light, and
the second image is a spectral image generated by combining green color data from which a yellow color component is eliminated and blue color data.

14. The endoscope system according to claim 10, wherein an image part inside the display switching area can be switched to one of the first image and the second image.

15. The endoscope system according to claim 10, wherein an image part outside the display switching area can be switched to one of the first image and the second image.

16. The endoscope system according to claim 10, wherein whether or not to move the display switching area by following a movement of a pointer can be set.

17. The endoscope system according to claim 10, wherein whether or not to display a pointer in the display switching area can be set.

18. An image display method, comprising:
generating a first image and a second image which have a coincident positional relationship with respect to a subject and are respectively obtained through different image processes; and
displaying the first image in an image part outside a display switching area in a display unit and switching an image part inside the display switching area to an image part, having a coincident positional relationship with the image part inside the display switching area of the first image with respect to the subject, of the second image.

* * * * *